United States Patent
Liu

(10) Patent No.: US 9,220,777 B2
(45) Date of Patent: Dec. 29, 2015

(54) ULTRASONICALLY-TRIGGERED DRUG VEHICLE WITH MAGNETIC RESONANCE IMAGING FUNCTION

(75) Inventor: Tse-Ying Liu, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 467 days.

(21) Appl. No.: 12/908,275

(22) Filed: Oct. 20, 2010

(65) Prior Publication Data

US 2012/0045397 A1    Feb. 23, 2012

(30) Foreign Application Priority Data

Aug. 17, 2010  (TW) ................................ 99127416 A

(51) Int. Cl.
*A61K 49/18*      (2006.01)
*A61K 9/00*       (2006.01)
*A61K 41/00*      (2006.01)
*A61K 9/127*      (2006.01)

(52) U.S. Cl.
CPC ........... *A61K 41/0028* (2013.01); *A61K 9/0009* (2013.01); *A61K 9/127* (2013.01); *A61K 9/1277* (2013.01); *A61K 49/1812* (2013.01); *A61K 49/1878* (2013.01)

(58) Field of Classification Search
CPC ............ A61K 9/00; A61K 9/14; A61K 9/127
USPC ............ 424/9, 9.1, 9.3, 43, 44, 450; 977/907, 977/915, 927, 773
See application file for complete search history.

(56) References Cited

U.S. PATENT DOCUMENTS

| | | | |
|---|---|---|---|
| 2003/0215394 A1 | 11/2003 | Short | |
| 2007/0071685 A1 | 3/2007 | Schneider et al. | |
| 2007/0081946 A1 | 4/2007 | Schneider et al. | |
| 2007/0258888 A1 | 11/2007 | Feldmann et al. | |
| 2008/0275330 A1 | 11/2008 | Mu et al. | |
| 2009/0098212 A1 | 4/2009 | Fossheim | |
| 2009/0130022 A1* | 5/2009 | Nishigaki et al. | 424/9.3 |
| 2009/0196827 A1 | 8/2009 | Wheatley | |
| 2010/0215587 A1 | 8/2010 | Huang | |
| 2010/0221190 A1 | 9/2010 | Bohmer | |
| 2010/0228122 A1 | 9/2010 | Keenan | |
| 2010/0247445 A1 | 9/2010 | Langereis et al. | |
| 2011/0059020 A1* | 3/2011 | Hirai et al. | 424/9.1 |

OTHER PUBLICATIONS

Robert C. MacDonald et al., Acoustically active liposomes for drug encapsulation fna ultrasound-triggered release, Biochemica et Biophysica Acta 1665 (2004), 134-141.*

Clive A. Prestidge et al., Silica nanparticle coated liposomes: A new type of hybrid nanocapsule for proteins, Interantional Journal of Pharmaceutics, 392 (2010) 285-293.*

Qingguo Xu et al. Encapsulation and relese of a hydrophobic drug from hydroxyapatite coated liposomes, Biomaterials, 28 (2007), 2687-2694.*

Jae-Hyun Lee et al. Dual-Mode Nanoparticle Probes for High-Oerformance Magnetic Resonance and Fluorescence Imaging of Neuroblastoma, Angew. Chem. Int. Ed. 2006, 45, 8160-8162.*

Hiroshi Shiho et al. Magnetic compounds as coatings on polymer particles and magnetic properties of the composite particles, J. Mater. Chem, 2000, 10, 333-336.*

Qingguo Xu et al. Encapsulation and release of a hydrophobic drgu from hydroxyapatite coated liposomes, Biomaterials, 28, (2007), 2687-2694.*

Huang, et al., "Ultrasound-triggered release behaviors of magnetic-liposome", National Yang-Ming University Institute of Biomedical Engineering, Master Thesis, Jul. 2010, 77 pages.

Bohmer, et al., "Ultrasound triggered image-guided drug delivery", European Journal of Radiology, 70, 2009, pp. 242-253.

Pisani, et al., "Perfluorooctyl Bromide Polymeric Capsules as Dual Contrast Agents for Ultrasonography and Magnetic Resonance Imaging", Advanced Functional Material, 2008, 18, pp. 2963-2971.

Huang, et al., "Acoustically active liposomes for drug encapsulation and utrasound-triggered release", Biomedica et Biophysica Acta 1665, 2004, pp. 134-141.

Lin, et al., "Factors Affecting Responsivity of Unilamellar Liposomes to 20 kHz Ultrasound", Langmuir, vol. 20, No. 15, 2004, pp. 6100-6106.

Schmitz, et al., "Image-guided focused ultrasound ablation of breast cancer: current status, challenges, and future directions", Interventional, Eur. Radiol, 2008 18, pp. 1431-1441.

Jain, et al., "Magnetic nanoparticles with dual functional properties: Drug delivery and magnetic resonance imaging", Biomaterials 29, 2008, pp. 4012-4021.

Sboros, "Response of contrast agents to ultrasound", Advanced Drug Delivery Reviews, 60, 2008, pp. 1117-1136.

Salomir, et al., "Local Delivery of Magnetic Resonance (MR) Contrast Agent in Kidney Using Thermosensitive Liposomes and MR Imaging-Guided Local Hyperthermia: A Feasibility Study In Vivo", Journal of Magnetic Resonance Imaging, 22, 2005, pp. 534-540.

Choi, et al., "Low-intensity ultrasound stimulates the viability and matrix gene expression of human articular chondrocytes in alginate bead culture", Wiley Periodicals, Inc., 2006, pp. 858-864.

* cited by examiner

*Primary Examiner* — Michael G Hartley
*Assistant Examiner* — Jagadishwar Samala
(74) *Attorney, Agent, or Firm* — Muncy, Geissler, Olds & Lowe, P.C.

(57) ABSTRACT

Present invention relates to an ultrasonically-triggered drug vehicle with magnetic resonance imaging function. In the delivery system of the invention, tracks the of drug vehicle carrying a certain drug (or drugs) is detectable by magnetic resonance imaging, and the release of drug is triggered by ultrasonication when the drug vehicle arrives at target site and accumulates to a desirable concentration. The MRI-guided drug delivery system provides improved accuracy of drug releasing, including position and timing.

9 Claims, 5 Drawing Sheets

(d)

| Conc. of vehicles | 1X | 2X | 3X | 5X |

HA-liposome

MHA-liposome-1x (a)

(b)

ULTRASONICALLY-TRIGGERED DRUG VEHICLE WITH MAGNETIC RESONANCE IMAGING FUNCTION

BACKGROUND OF THE INVENTION

Current ultrasound-guided drug delivery systems mainly use commercial ultrasound contrast agent to carry drugs, for which the ultrasound contrast agent may performance the function of trafficking and ultrasonically-triggered drug releasing. However, the mentioned drug delivery systems might encounter following issues: (1) "Background leakage", that is, the leakage of drugs from the vehicle during the storage process, or in the in vivo circulation process before reaching and being triggered at target site; and (2) "seeing" the contrast agent at non-affected area in a series of image acquisition, the drug may also be released by the triggering at non-affected area, which makes the mentioned drug delivery method more difficult to control the timing and location of release. Therefore, in addition to medical diagnostic ultrasound, it is necessary to find a new medical imaging technology for vehicle's tracking.

Another known technology relates to the use of MR image-guided focus ultrasound to achieve site-specific drug delivery. It uses magnetic resonance imaging to guide ultrasound equipment for the energy focusing position, so that ultrasound can be projected and focused on a specific location. By the ultrasonic energy, the vascular barrier at a specific location will be opened temporarily or the permeability of tissue will be increased, so that the drug delivered to the area by circulation can successfully penetrate the barrier and get into the affected tissues. However, in that technology, drugs do not be encapsulated in a vehicle, which may be confronted with the problems that (1) drugs will enter the systemic circulation and produce side effects, for anticancer drugs with higher toxicity; and (2) certain drugs having short half-life in blood may be non-effective before reaching the target area.

The third conventional drug delivery involves the use of single crystal iron oxide as the magnetic shell structure to lower the leakage of drugs, and the use of "alternating magnetic field" to generate changes in the volume of shell material (i.e., magnetostriction), resulting in cracked ferric oxide shell and drug release (Adv. Mater. 2008, 20, 2690-2695). However, there are problems in above drug delivery to limit its application: (1) the technology needs an alternating magnetic field of high-intensity to trigger drug delivery, and there is no commercially available medical equipment so far, for that the safety to human body is still unable to verify, and the temperature in tissues is more difficulty to be controlled; (2) it is uncertain whether the magnetic shell used in the technology is superparamagnetic, where the superparamagnetism is an important characteristic of MRI T2 imaging; (3) it is unknown if there are any magnetic resonance imaging (MRI) signal changes of the vehicle could be induced after the triggering in magnetic field, or impossible to examine the state of vehicle by the MRI signal variations; (4) although the method may be combined with "MRI" and "magnetism-controlled drug delivery", the drug delivery device actually can not be integrated with the magnetic resonance imaging equipment, because the main field for MRI is a static magnetic field, and the intensity of radio frequency electromagnetic field is too low, both of which are unable to produce the required alternating magnetic field to carry out the magnetism-controlled drug release, making diagnosis and treatment of that method hardly be conducted on the platform of MRI device; and (5) generally the "magnetically-triggered drug vehicle" must take magnetic field-triggering for drug release, whereas the use of electromagnetic field as a triggering energy may result in a risk of health, for that electromagnetic field is not easy to precisely focus and directionally spread, and probably is a quite interference to general medical equipment.

Based on the consideration of the disadvantages mentioned above, the inventor invents to combine "magnetic resonance imaging", "ultrasonically-triggered drug release" and "low background leakage" in a drug vehicle structure that can track the image of drug delivery vehicle by MRI to confirm if adequate amount of which reach to a specific location, and trigger the drug release from delivery vehicle immediately by ultrasound to achieve the precise administration of treatment, and avoid the lower dosage efficiency caused by the patient's movement or the time difference, which may result in different conditions at the time of triggering from which at imagining. Although the combination of MRI and ultrasound had been described in clinical cases of commercial medical device, which cases mainly using MRI-guided ultrasound to focus and conduct burning therapy on tumor, no prior art ever disclosed a drug delivery method by using MRI to track vector images, and the subsequent use of ultrasound to trigger drug release.

SUMMARY OF THE INVENTION

This invention has developed an ultrasonically-triggered drug vehicle exhibiting magnetic resonance imaging function with extremely low background leakage. The present drug vehicle can significantly reduce the "background leakage" level of general high polymer ultrasound contrast agents, perform the vehicle image tracking through MRI, and ultrasonically trigger the release of drug when the vehicle has reached target site and accumulate to a sufficient treating concentration, so that significantly increase the precision of the location and timing of drug release, reduce the drug dosage and side effects, and enhance the effect of chemotherapeutic drugs through the original properties of ultrasound in speeding drug penetration and absorption (i.e., sonophoresis), and in raising the temperature in tissues.

In one aspect, the present invention features an ultrasonically-triggered drug vehicle, which comprising: a polymeric microsphere (as a core) for carrying drug; and an inorganic shell with bio- and hemo-compatibility, wherein the surface of the inorganic shell is decorated with independent superparamagnetic iron oxide nano-particles.

In one embodiment of the invention, the polymeric microsphere is a solid or hollow core possessing biomedical compatibility, and may carry drugs in the sphere previously. In another embodiment, the inorganic shell may be of a biocompatible (including hemo-compatible) ceramic material made by chemical synthesis in aqueous solution, the main function of which is to increase the resistant ability against background leakage, and to improve the vehicle sensitivity to high-frequency ultrasound. In a further embodiment, the outer shell of the vehicle is a thin and inelastic inorganic nano-shell, which may be broken under the medical diagnostic ultrasound of high frequency (1-10 MHz or above) and low power density (below 0.5 W/cm$^2$).

One feature of the present invention is the use of co-precipitation to cover a layer of biocompatible and/or hemocompatible inorganic shell on to as well as making polymers with the external surface of the polymeric microsphere, and to decorate the inorganic shell with superparamagnetic nano-particles. Although the third drug delivery technology mentioned above proposed the use of single crystal iron oxide as a magnetic shell, but the synthesis method of which involves direct formation of the single crystal iron oxide shell on the polymeric sphere, and in relevant literatures, there is no description or disclosure about the superparamagnetism demonstrated by the shell.

In one embodiment, the superparamagnetic nano-particles may be biocompatible superparamagnetic materials chemically synthesized through room temperature aqueous solution, which will provide a imaging contrast function for comparing magnetic resonance image T2 (T2=1/R2) and T2* (T2*=1/R2*), and control the slope (r2 and r2*) in the plotting of R2 and R2* vs vehicle concentration by the amount of SPIO nano-particles; besides, when vehicle is triggered by ultrasound, its structure will rupture to cause changes in dispersion of the superparamagnetic nano-particles, thereby alter the nonuniformity in magnetic field. Therefore, there will be differences between T2 and T2* contrast signals before and after the action of ultrasound, which means that the R2*–R2 slope difference ratio ((r2*–r2)/r2*) will be changed after the ultrasound triggering, and the changing extent of this difference ratio will be increased with the reduced numbers of SPIO. These phenomena can be used as references for judging the state of vehicles (where it is triggered to release drugs).

In another aspect, the present invention features a method of ultrasonically-triggered drug delivery, which comprising: administrating a drug vehicle including a polymeric microsphere (in which carrying drugs), and a bio- and hemo-compatible inorganic shell decorated with independent superparamagnetic iron oxide nano-particles on its surface to a subject in need thereof; tracking the image of drug vehicle through magnetic resonance imaging (MRI); and triggering drug release from vehicle by ultrasound (as triggering energy) when the vehicles reach a specific location and accumulate to effectively treating amount of which.

The method is characterized that the vehicle exhibits MR contract function, the drug release will not be triggered during the imagine tracking, but only triggered by ultrasound after conforming the vehicle distribution through MRI; and that the drug releasing state of vehicles can be further detected with changes in magnetic resonance signals caused by the structural change of drug vehicles. In one embodiment of the invention, commercially available medical diagnostic ultrasound can be used for triggering drug release, and the temperature in tissues can be controlled through the duty ratio of controller, so the method of this invention can be carried out with the existing equipments. In addition, the MRI and the immediately following drug release triggered by ultrasound comprised in the present method can be done on the same device platform, which will not produce different conditions between imaging and triggering caused by the motion of the patient, resulting in lower efficacy of treatment.

Other features or advantages of the present invention will be apparent from the following drawings and detailed description of several embodiments, and also from the appending claims.

DETAILED DESCRIPTION OF THE INVENTION

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Example

Figure 1:
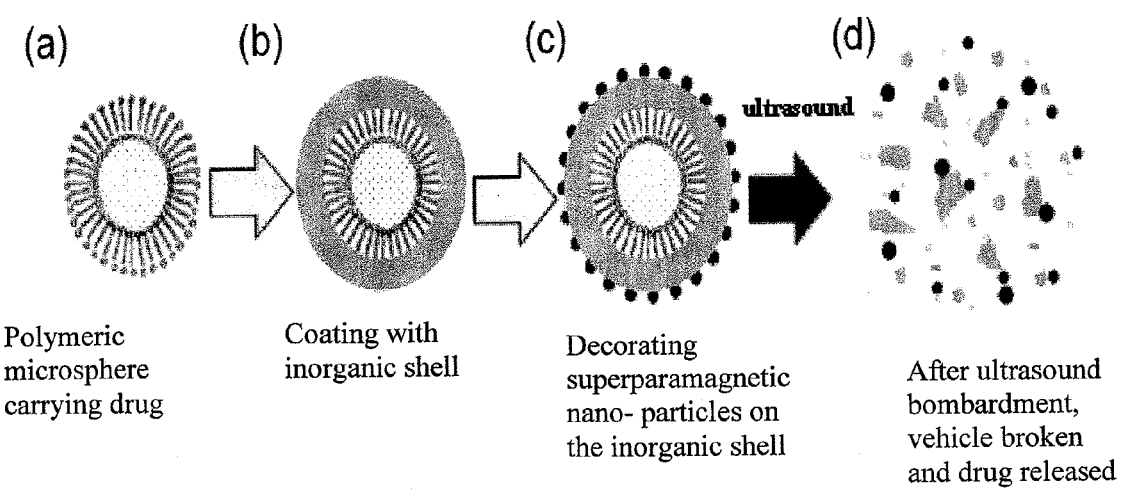
FIG. 1 is a schematic drawing showing the structure and action principle of one embodiment of the ultrasonically-triggered drug vehicle with magnetic resonance imaging function of this invention.

As showed in FIG. 1, the drug vehicle structure of this invention includes a polymeric microsphere (core) for carrying drug(s); and a biocompatible and/or blood-compatible inorganic shell, and the shell is decorated with independent superparamagnetic iron oxide nano-particles on its surface.

In which, the polymeric microspheres used to carry drug (FIG. 1a) may be liposomes, micelles of amphiphilic polymer, or general solid or hollow microspheres with biomedical compatibility; as required, size of the microspheres may be controlled in the range of 50 nm to 2000 nm through the manufacturing process technology. The inorganic shell may be made of hydroxyapatite, zinc oxide (ZnO), silica ($SiO_2$), copper oxide (CuO), or other biocompatible (including blood-compatible) ceramic materials produced through aqueous solution chemistry; as required, thickness of the inorganic shell may be in the range of 10 nm to 60 nm through the regulation of the process conditions.

Figure 2:
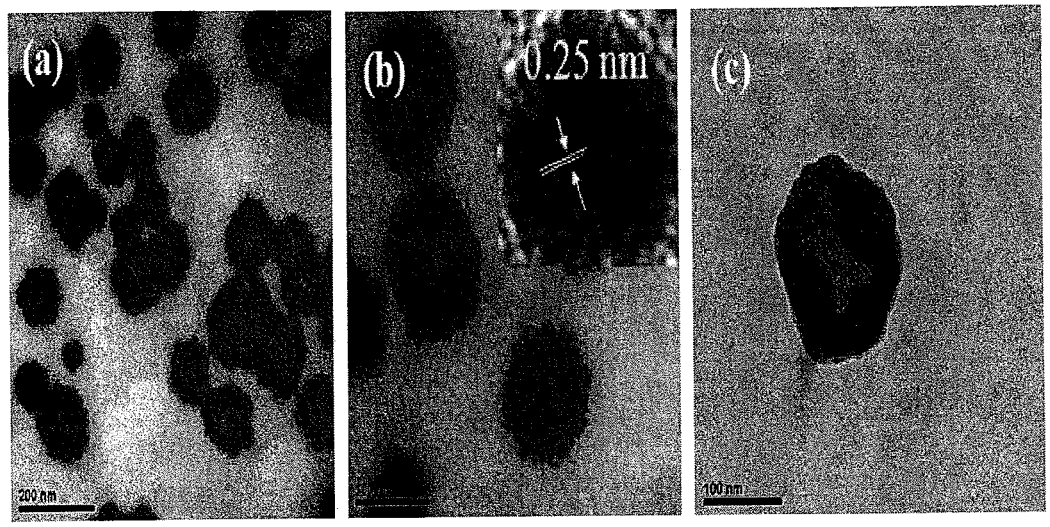
FIG. 2(a) shows the transmission electron microscope (TEM) image of drug vehicle having liposome coated with a layer of hydroxyapatite inorganic shell without decorating SPIO nano-particles (HA-liposome)
FIGS. 2(b) and (c) show the high resolution transmission electron microscope (HR-TEM) images of drug vehicles having various SPIO nano-particle numbers decorated on the hydroxyapatite shell structure (MHA-liposome), wherein (b) vehicles having lower number of SPIO (MHA-liposome-1×), HR-TEM image of SPIO nano-particle is shown in the right upper inset, in which the interplaner spacing of $Fe_3O_4$ (311) plane of 0.25 nm was observed; (c) vehicles having higher number of SPIO (MHA-liposome-10×)
FIG. 2(d) shows the MR T2 contrast image, wherein the HA-liposome vehicle was used as control group, and four concentrations (1×, 2×, 3× and 5×, respectively) of the MHA-liposome-1× vehicle were taken as experimental groups.
Figure 2:
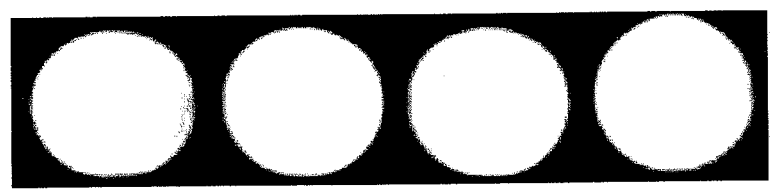
Figure 2:

In the present invention, a co-precipitation method is used to deposit an inorganic shell with biomedical compatibility and blood compatibility on the surface of polymer microspheres (FIG. 1b), and to decorate the inorganic shell with superparamagnetic nano-particles on its surface, synchronously, to form the structure of drug delivery of this invention (schematically showed in FIG. 1c, actual electron microscope image showed in FIGS. 2b and 2c). The superparamagnetic nano-particles decorated on the inorganic shell (as showed in FIG. 2b right upper inset) may be superparamagnetic iron oxide (SPIO) nano-particles, or may be made of ferric platinum (FePt), or of other biocompatible superparamagnetic material produced through room temperature aqueous chemical synthesis; of size ranging below 10 nanometers. On the surface of the structure of present drug vehicle, there decorated with superparamagnetic nano-particles (FIG. 2b), which obtained the MRI T2-weighted images as shown in FIG. 2d.

The method for producing a preferable embodiment of the present drug vehicle is described as following:

1. Preparation of Liposomes

In this embodiment, 1,2-diacyl-sn-glycero-3-phosphocholine was used as the raw material for preparing of liposomes. 25 mg of lecithin was taken into a 20 ml sample bottle, 1 ml of methanol solution was added to completely dissolve the lecithin, and homogenized by vortex mixer. The resultant solution was incubated in an oven setting at 50° C. After the solution was completely dried in the bottle, 10 ml of Xylenol Orange (XO; as the model drug) aqueous solution was added, and the mixture was shaken with ultrasonic homogenizer to form liposomes. Finally, the non-encapsulated drugs were removed by gel column chromatography.

2. Preparation of Liposomes Having SPIO Nano-Particles Decorated on Hydroxyapatite Inorganic Shell (MHA-Liposome)

A solution of liposome carrying Xylenol Orange as described above was prepared previously. 3 ml of aqueous ammonia was slowly added to the liposome solution, and each 400 μl of $2.9 \times 10^{-2}$ M calcium acetate aqueous solution, $2.3 \times 10^{-2}$ M ferrous chloride aqueous solution, and $1.7 \times 10^{-2}$ M phosphate solution were added dropwise, and then uniformly stirred for 10 minutes. Repeat the above steps for five times. After centrifugation, the precipitate was dispersed in water. The molar ratio of $X_{Ca/P}=1.67$, $X_{Ca/Fe}=0.8$ were kept constant, so as to cover a layer of hydroxyapatite (HA) inorganic nano-shell decorated with SPIO nano-particles on the surface of liposomes, to form the so-called MHA-liposomes, which is an applicable ultrasonically-triggered drug vehicle with magnetic resonance imaging function.

In addition, by controlling the concentration of precursor, obtained drug delivery vehicles decorated with various number of SPIO nano-particles. For instance, vehicles with smaller number of SPIO (called MHA-liposome-1×; FIG. 2b) were obtained under the above parameters. Vehicles with larger number of SPIO (called MHA-liposome-10×; FIG. 2c) were obtained when the concentration of above precursor was increased by ten times (that is, each 400 μl of $2.9 \times 10^{-1}$ M calcium acetate solution, $2.3 \times 10^{-1}$ M ferrous chloride solution and $1.7 \times 10^{-1}$ M phosphate solution were added) SPIO can be a number of carriers, called MHA-liposome-10×.

The manufacturing method of the drug release vehicle is characterized by that the biocompatible inorganic shell and the superparamagnetic iron oxide nano-particles are co-deposited on the polymeric spheres, and in the synthesis process, independent superparamagnetic nano-particles are decorated on the surface of the inorganic shell by controlling the growth kinetics of nucleation, so confers the superparamagnetic particles a function as MRI T2 contrast agent.

The outer shell of the drug vehicle is of thin, dense and inelastic inorganic nano-shell, it can prevent leakage of drugs in the absence of ultrasound function. The structure of vehicle can be rapidly destroyed under the medical diagnostic ultrasound bombardment of high frequency (1-10 MH) and low power density (0.5 W/cm² or less) owing to the hard and brittle nature of inorganic shell, which results in cracking the drug delivery structure and no longer assembling, but promoting quick release of the drug from the inside of polymeric microsphere (as shown in FIG. 1d). These characteristics make the present drug vehicle superior to conventional "polymeric nano-carriers", for that conventional nano-scaled liposomes or polymeric ultrasound trigger carriers must be triggered effectively under low frequency (20-40 kHz).

A background leakage test was carried out in the following methods. The drug vehicles were dispersed in 10 ml of double distilled water, the vehicles and water bath were separated by dialysis membrane to prevent the interference of vehicles to spectral measurements. Seven-day naturally continuous release experiment was performed, sampling at intervals of two days. At the end of experiment, the absorbance at 431 nm of the drug in the water bath was measured by a UV/visible spectrophotometer. The obtained absorbance value was substituted into the calibration curve, for calculating the concentration of drug release, and the drug background leakage data (Cumulative release amount, CRA) was obtained by the following formula.

$$CRA = M_{e,t}/M_{e,max}$$

$M_{e,t}$: accumulated concentration of drug released by vehicle at day 1, 3, 5, and 7.

$M_{e,max}$: drug releasing after disruption of vehicle.

Figure 3:
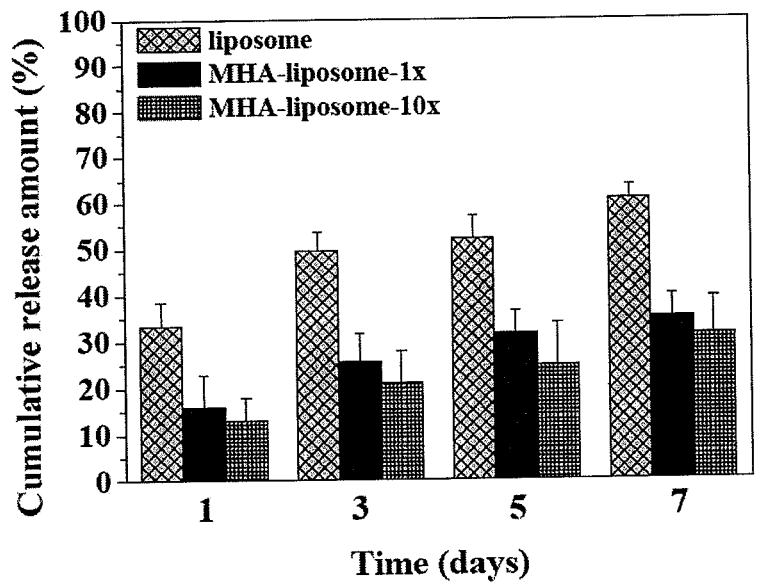
FIG. 3(a) shows comparative diagram of background leakage in the present drug vehicle with liposome; and (b) shows comparative results of the present drug vehicle with liposome in the sensitivity to ultrasound, ultrasonic frequency: 3 MHz, power density: 0.2-1 W/cm².
Figure 3:
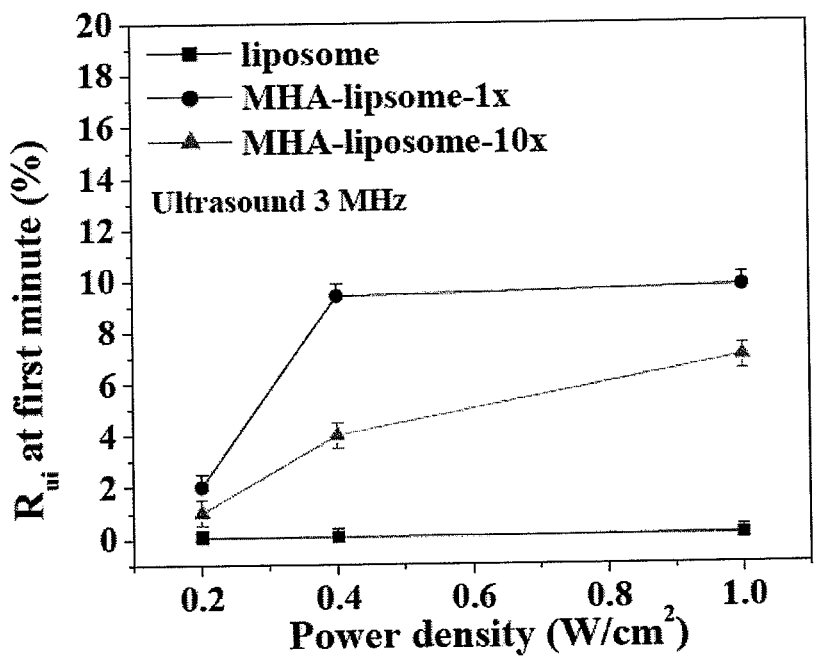

The results indicated that, comparing to non-modified liposomes, the drug vehicles obtained by the invention exhibit excellent resistance to background leakage (FIG. 3a), and can promote fast drug release after being triggered by ultrasound (3 MHz, 0.4 W/cm²) as the breaking of vehicles (FIG. 3b). Before applying the triggering action of ultrasound to drug vehicles of the invention, the super-paramagnetic nano-particles decorated on the inorganic shell play an action of MRI T2 contrast feature, which make it possible to track the vehicle image through magnetic resonance imaging, and to control the location and timing of drug release more precisely. This feature can be regulated by adjusting the quantity of SPIO nanoparticles, which may be illustrated by comparing FIGS. 4a and 4b. When the number of SPIO was varied from 1-fold to 10-fold, the slope of R2 and R2* both increased significantly.

Figure 4:
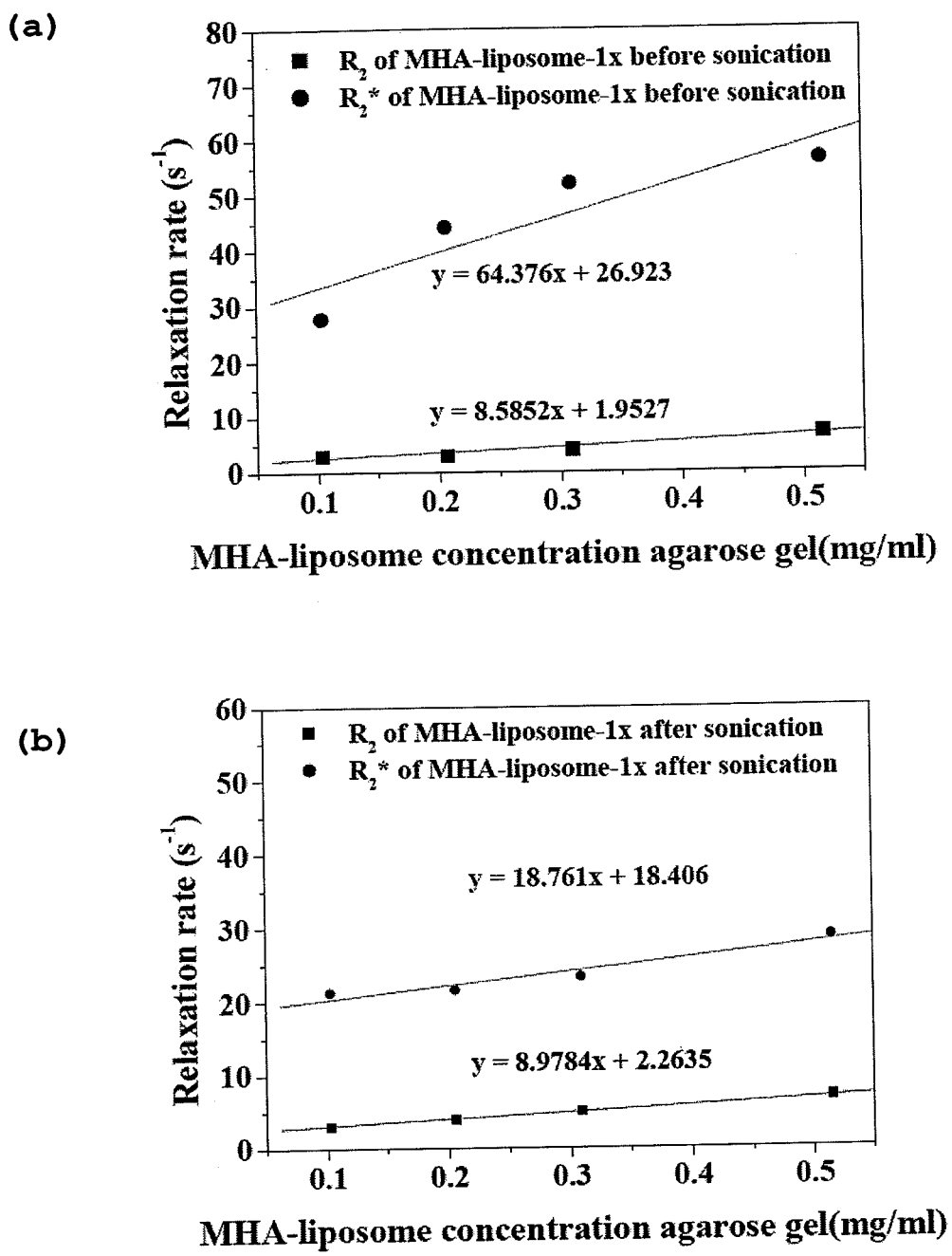
FIG. 4 shows the R2-R2* mapping of liposomes coated with MHA before and after the triggering by ultrasound, in which the significant changes in slope difference (r2*–r2) between R2 and R2* can be observed before (FIG. 4(a)) and after (FIG. 4(b)) the ultrasound bombardment (MHA-liposome-1× samples); in 4(c) and 4(d) the same phenomenon also be observed for MHA-liposome-10× samples.
Figure 4:
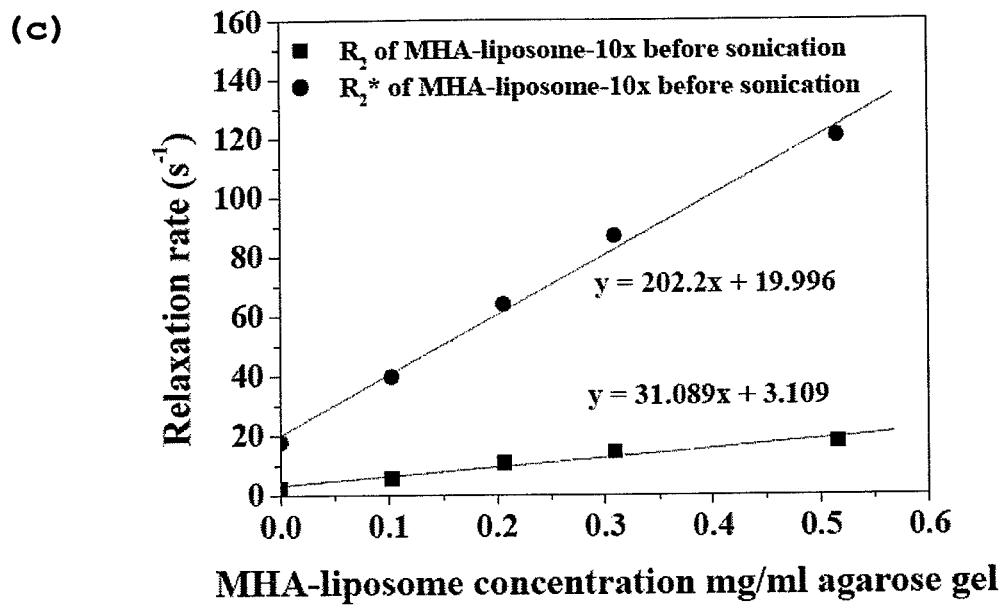
Figure 4:
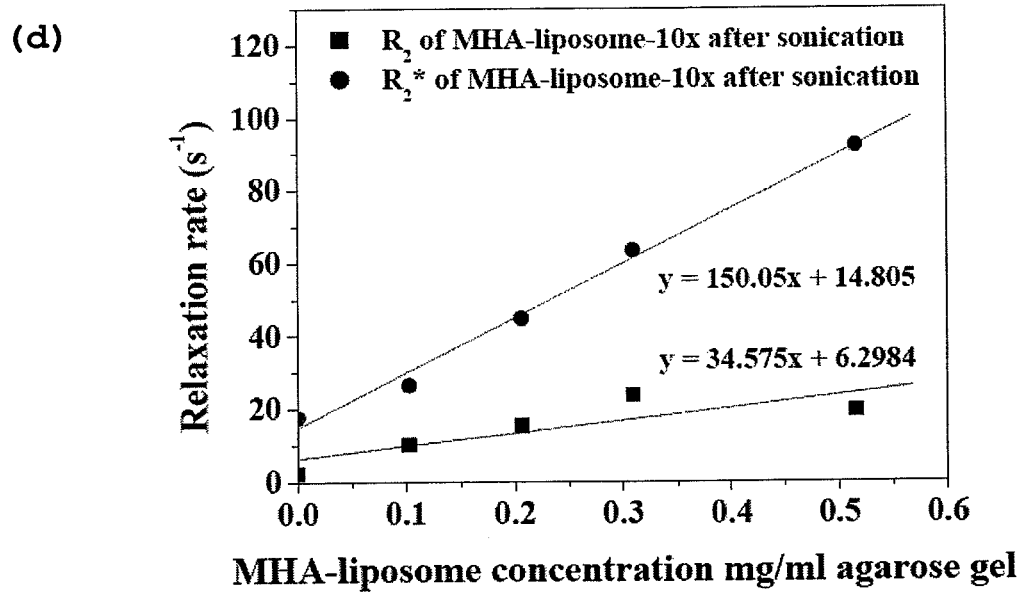

Additionally, as shown in FIG. 4, when the concentration of vehicle accumulated to sufficient amount in a specific target position, the vehicle structure will be ruptured after ultrasound triggering, which caused the dispersion of superparamagnetic nano-particles to change, resulting in the variation in the distance and distribution level of superparamagnetic nano-particles, and also alter the nonuniformity in the magnetic field, so that MR signals generate significant changes in the difference value between R2* slope and R2 slope. For example, as shown in FIGS. 4a and 4b, difference value between R2*-R2 slopes was reduce in specimen MHA-liposome-1× after the ultrasound bombardment, and as shown in FIGS. 4c and 4d, the reducing phenomenon was also observed in specimen MHA-liposome-10×; Furthermore, the reduce level of difference value in R2*-R2 slope will be increased as reducing the number of SPIO nano-particles, these mentioned phenomena exhibited by the present invention can be used as references for judging the state of vehicles.

In summary, the ultrasound triggered drug delivery system of the invention combines MRI tracking of vehicles with in vitro ultrasound triggered drug release, which can effectively improve the precision of administration position and timing at target site, and reduce the toxicity of chemotherapeutic drugs to normal tissues. Also, the drug releasing methods of this invention uses ultrasound as the triggering energy, is enable to trigger vehicle breaking and drug release by using medical diagnosis ultrasound, which has been highly commercialized. The medical ultrasound with high security also has advantages of energy focusing, precise directional transmission, deeply penetrating soft tissue and the like.

Furthermore, ultrasound has the function of accelerating drug penetration and absorption, which has been widely used in clinical treatment for transdermal administration, cancer treatment and physical therapy. In addition, the medical fields have clinical experience in integrating the diagnostic ultrasound into magnetic resonance imaging equipments. Therefore, the technology described in the present invention can be practiced by using existing equipments, and is an invention possessing both practicability and safety.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An ultrasonically-triggered drug vehicle with magnetic resonance imaging function, which comprises:
    a polymeric microsphere core for carrying drug; and
    a co-precipitation structure covering the polymeric microsphere core, consisting of an inorganic shell with bio- and hemo-compatibility and independent superparamagnetic nano-particles decorating on the inorganic shell,
    wherein the inorganic shell is made of a material selected from the group composed of hydroxyapatite, zinc oxide (ZnO), and copper oxide (CuO) and broken under the ultrasound bombardment of high frequency (1-10 MH) and low power density (below 0.5 W/cm2), and the superparamagnetic nano-particles are superparamagnetic iron oxide (SPIO) nano-particles or ferric platinum (FePt) nano-particles.

2. The ultrasonically-triggered drug vehicle of claim 1, which has a magnetic resonance imaging function to conform the vehicle distribution through magnetic resonance imaging (MRI) at the time of imaging tracking.

3. The ultrasonically-triggered drug vehicle of claim 1, wherein the polymeric microsphere core is selected from the group composed of liposomes, micelles of amphiphilic polymer, and solid or hollow microspheres with biomedical compatibility.

4. The ultrasonically-triggered drug vehicle of claim 3, wherein the polymeric microsphere core has particle size of 50 nm to 2000 nm.

5. The ultrasonically-triggered drug vehicle of claim 1, wherein the thickness of the inorganic shell is in the range of 10 nm to 60 nm.

6. The ultrasonically-triggered drug vehicle of claim 1, wherein the superparamagnetic nano-particle has particle size less than 10 nm.

7. A drug delivery method by ultrasonically-triggered vehicle, which comprises the step of:
    administrating the ultrasonically-triggered drug vehicle of claim 1 to a subject in need thereof;
    tracking the image of drug vehicle through magnetic resonance imaging (MRI); and
    triggering drug release by ultrasound (as triggering energy) when the vehicle reaching to target site and accumulating to effective amount of treatment.

8. The method of claim 7, wherein the vehicle is bombarded by ultrasound of high frequency (1-10 MH) and low power density (below 0.5 $W/cm_2$), which results in cracking the drug vehicle structure and no longer assembling (or recoating) to release the drug.

9. The method of claim 7, which further comprises the step of detecting drug releasing state of the vehicle through the variation in magnetic resonance (MR) signal caused by the structural change of the drug vehicle.

* * * * *